United States Patent [19]

Bogue et al.

[11] Patent Number: 4,916,629
[45] Date of Patent: Apr. 10, 1990

[54] METHOD FOR DETERMINATION OF PITH LOCATION RELATIVE TO LUMBER SURFACES

[75] Inventors: David N. Bogue, Tacoma; Charles F. Horn, Puyallup; Steven L. Washburn, Federal Way; Stanley L. Floyd, Enumclaw, all of Wash.

[73] Assignee: Weyerhaeuser Company, Tacoma, Wash.

[21] Appl. No.: 198,101

[22] Filed: May 31, 1988

Related U.S. Application Data

[63] Continuation-in-part of Ser. No. 67,334, Jun. 26, 1987, Pat. No. 4,831,545.

[51] Int. Cl.[4] .................. B27B 1/00; G01N 21/88; G06F 15/46
[52] U.S. Cl. .................... 364/507; 364/551.01; 356/237; 250/563; 144/356
[58] Field of Search ............... 364/507, 556, 570, 550, 364/511, 559; 83/365, 72, 73; 356/239, 237, 364, 384, 376, 445, 446; 250/560, 562, 563, 572, 223 R; 144/356, 357; 156/64

[56] References Cited

U.S. PATENT DOCUMENTS

| | | | |
|---|---|---|---|
| T932,008 | 3/1975 | Davis et al. | 250/571 |
| 3,120,861 | 2/1964 | Finlay et al. | 144/2 R |
| 3,329,181 | 7/1967 | Buss et al. | 144/2 R |
| 3,391,501 | 6/1970 | Barr et al. | 51/281 R |
| 3,942,021 | 3/1976 | Barr et al. | 250/572 |
| 3,976,384 | 8/1976 | Matthews et al. | 356/431 |
| 3,983,403 | 9/1976 | Dahlstrom et al. | 250/560 |
| 4,123,702 | 10/1978 | Kinanen et al. | 324/58.5 A |
| 4,149,089 | 4/1979 | Idelsohn et al. | 250/563 |
| 4,163,321 | 8/1979 | Cunningham | 33/15 |
| 4,188,544 | 2/1980 | Chasson | 250/560 |
| 4,207,472 | 6/1980 | Idelsohn et al. | 250/563 |
| 4,221,974 | 9/1980 | Mueller et al. | 250/563 |
| 4,281,696 | 8/1981 | Howard et al. | 144/357 |
| 4,286,880 | 9/1981 | Young | 356/431 |
| 4,482,250 | 11/1984 | Hirvonen et al. | 356/369 |
| 4,541,722 | 9/1985 | Jenks | 356/376 |
| 4,606,645 | 8/1986 | Matthews et al. | 356/446 |
| 4,607,212 | 8/1986 | Jakkula | 324/58.5 R |
| 4,831,545 | 5/1989 | Floyd et al. | 364/507 |

Primary Examiner—Felix D. Gruber
Assistant Examiner—V. N. Trans

[57] ABSTRACT

The invention is a method of assisting lumber grading using an electro-optical scanning system. A first critical determination is determination of pith position of the log from which the lumber was cut, relative to the scanned faces. This then indicates knot orientation. With knot orientation known, knot size and position data also determined by the scanning system can be used to accurately estimate cross sectional area of the knots. From this point a tentative lumber grade can readily be assigned. Pith position is indicated by a number of factors including wane, knot counts on each of the faces and the presence or absences of spiky faces. A preferred form the scanner is one which measures localized wood fiber angles relative to three orthogonal axes. These fiber angle measurements reveal grain slope disturbances on the lumber which are indicative of many types of defects including knots. The system has been used for grading lumber at speeds as high as 350 m/min. with considerable accuracy.

6 Claims, 6 Drawing Sheets

METHOD FOR DETERMINATION OF PITH LOCATION RELATIVE TO LUMBER SURFACES

This application is a continuation-in-part of application Ser. No. 067,334, filed June 26, 1987, now U.S. Pat. No. 4,831,545.

BACKGROUND OF THE INVENTION

The present invention is an automated method for assisting lumber grading. It involves determination of the pith location of the log from which the lumber was cut relative to the lumber surfaces. Having this knowledge, the orientation of knots within the lumber can be ascertained and the cross sectional area of the knots more readily estimated. In its most preferred form, the method assigns a tentative grade to the lumber.

Several criteria are used in grading lumber products. Lumber to be used for furniture, mill work or similar products is graded on the basis of appearance with relatively little consideration being given to defects which could affect strength. On the other hand, appearance is given essentially no weight in grading lumber products intended for structural use. The lumber grades are assigned on the basis of the expected strength in bending, compared with that of similar defect-free products. Most grading rules in the United States are based on ASTM Test Method D 245-81. This publication notes that lumber grades "designate near-minimum strength and near-average stiffness properties on which to base structural design."

Virtually all structural lumber today is visually graded. This is done by examining all four faces and the ends of the piece and by noting the location as well as the size and nature of knots and other defects over the entire length. As noted earlier, lumber grades are based on the strength ratio of a structural member compared to the strength it would be expected to have if no weakening characteristics were present. The various factors that affect strength are knots, grain deviations such as diving grain, shake, and checks or splits. Certain other factors such as various types of warpage, density, and the presence or absence of surface defects such as planar skip or wane also enter into the grading process.

Most structural lumber in the United States is graded with the assumption that it will be used as a joist; i.e., with bending loads applied to one of the narrow faces of the lumber. Other grading rules apply to lumber designated for use as planks; i.e., with the bending load applied to one of the wide faces. Some lumber is graded for use in compression, wall studs being an example.

While all of the defects noted previously are important, the presence of knots is generally the principal reason for downgrading lumber. To again quote from ASTM D-245 "Strength ratios associated with knots and bending members have been derived as the ratio of moment-carrying capacity of a member with cross section reduced by the largest knot to the moment-carrying capacity of the member without defect. This gives the anticipated reduction in bending strength due to the knot. For simplicity, all knots on the wide face are treated as being either knots along the edge of the piece (edge knots) or knots along the centerline of the piece (centerline knots)." Thus, in grading a piece of lumber the grader must visually and very rapidly note the number, size and position of knots, estimate their cross sectional area, and mentally determine how much they will reduce the strength of the piece. In addition, he must also factor in all of the other flaws which affect grade. He must do all of this in a period of only a few seconds, mark the grade on the lumber and then move on to the next piece.

Grading is a job that requires very high skill. Graders are routinely examined by a head grader from one of the industry supported grading bureaus and are typically required to assign correct grade at least 95% of the time.

In the past, many attempts have been made at machine grading lumber. Probably the simplest of all methods is to bend the lumber as a plank in flexure and determine modulus of elasticity. Pieces that fall below a given threshold level are diverted to the lower grades. Other more sophisticated methods involve scanners which determine the presence and location of knots and/or other defects and assign a grade on this basis. One group of scanners detects knots on the basis of their color in comparison to the adjacent wood. Stated otherwise, scanning is based on a gray scale with the darker colors representing knots and the lighter colors representing knot-free wood. One early method is disclosed in U.S. Pat. No. 3,120,861 to Finlay et al. Another group of automated graders also involves human intervention with the scanning system. One such method is described in U.S. Pat. No. 3,329,181 to Buss et al. Here a human inspector marks the flaws prior to scanning and may input information to the computer describing the nature of the flaw; e.g., that it might be acceptable in some lumber grades and unacceptable in others. Barr et al in U.S. Pat. Nos. 3,931,501 and 3,942,021 include in their background a good description of prior art scanners which are associated with a computer for decision making. The Barr scanners also require human input for designating the defect type which must be marked on the board prior to scanning. In this system the scanner unit moves along the workpiece and uses an ultraviolet light and photocell array to detect defects, including those marked by the inspector. U.S. Pat. No. 4,163,321 to Cunningham relates closely to the system of Barr et al.

Another scanning system for grading lumber which requires human intervention is described in U.S. Pat. Nos. 4,149,089 and 4,221,974 to Mueller et al. The Mueller system uses a swept laser beam to examine both faces of a board. A human inspector serially inputs the class of flaw to the computer as it passes the scanning station. The human inspector may enhance a flaw for detection by the scanner or may suppress certain characteristics which the scanner might detect as an objectionable flaw. The computer then makes optimum cutting decisions by comparing the board characteristics with an order file. U.S. Pat. Nos. 4,149,089 and 4,207,472 to Idelsohn and U.S. Pat. No. 4,286,880 to Young show systems which are similar in many respects to those described by Mueller et al.

The prior art systems noted to date are predominantly interested in detecting defects which affect the visual appearance of wood and little emphasis is placed on defects which affect structural properties. In these systems the wood is primarily intended for use in furniture manufacture and may be very high value hardwoods so that optimum cutting decisions for remanufacture can be of great economic importance.

A somewhat different type of scanner for wood is disclosed in PCT Application No. WO85/00657. Here the scanners examine at least one end and one longitudinal surface. One set of sensors have coarse resolution while another set has fine resolution. The fine resolution sensors are capable of movement so that they can examine specific areas of the lumber noted by the other sensors. This also is a gray scale scanner. However, the inventors note that other defects besides knots, such as pith streaks, can be recognized.

A different scanning system is disclosed in U.S. Pat. No. 3,976,384 to Matthews et al. Here light is injected into the surface of lumber at one point and the emerging light is detected at a spaced apart location. The system can detect defects such as knots, blue stain, and certain types of rot. The inventors have noted that in clear (defect free) wood, light traveling across the grain is attenuated by a factor almost 50 times greater than light traveling along the grain. The method senses surface fiber direction changes on the plane of the face being measured. However, it has been found to be unsuitable for use on the woods of deciduous, or so-called "hardwood," species.

Another type of system using microwave scanning is found in U.S. Pat. Nos. 4,123,702 to Kinanen et al and 4,607,212 to Jakkula. Kinanen uses high frequency microwave energy to detect knots based on their differing dielectric constant from sound wood. Jakkula similarly uses microwave radiation to detect knots by noting a mode or polarization shift from TEM to TM which is detected by a receiver. This inventor notes that knots can be detected in a wane edge but does not comment further on the this observation.

Another group of Finnish inventors, Hirvonen et al, in U.S. Pat. No. 4,482,250 scan a wood surface with a polarized beam of light having the plane of polarization either parallel to or perpendicular to the longitudinal axis of the piece of wood. The light reflected from a piece of sound wood is only partially depolarized while the light reflected from a knot is almost totally depolarized.

Davis et al, in U.S. Defensive Publication No. T932,008 disclose an optical system for measuring surface fiber direction in a moving web structure. These authors note that when collimated light is projected on a fibrous web, the light will be reflected with greatest intensity perpendicular to the fiber axes. Reflectance values measured along and across the machine direction of the web can be used to determine the average orientation of the fiber on the surface in two dimensions.

An advanced scanner which can determine fiber angle in three dimensions from a surface examination is described in Matthews et al, U.S. Pat. No. 4,606,645. This is commonly assigned with the present invention and is incorporated herein by reference. This Matthews invention measures fiber angle in a fibrous solid material relative to three mutually orthogonal reference axes. It is particularly well suited from measuring diving grain and grain surface angle in wood. This scanner employs a laser beam which may be mechani-optically swept transversely across the surface of a longitudinally moving piece of lumber. Reflections from the surface are measured by an array of photo detectors lying preferably in a common plane around the illumination source. The method can very readily pick up aberrations in grain angle such as those caused by knots below the surface or by visible knots. Additionally, it can readily detect other defects such as planar skip, wane, and splits.

Other scanners have been concerned with detection of wane on lumber. Wane is here defined as an original unsawn surface of the log which truncates one or more edges of the piece of lumber. U.S. Pat. No. 3,983,403 to Dahlstrom et al describes a system for detecting and measuring wane. Another system which can recognize wane is described in U.S. Pat. No. 4,188,544 to Chasson.

While all of the above-noted inventions are useful in some way for scanning wood surfaces and providing quality information, none of them have been developed into apparatus which can do structural grading at the very high speeds required in a modern lumber mill. In fact, those which require human intervention are in many cases no faster or more accurate than visual grading. The present invention has overcome the problems inherent in the prior art methods and is capable of accurately grading structural lumber at the high speed found in modern sawmills. In advanced versions of the invention, no further human intervention is necessary, while in simpler versions a tentative grade is proposed which may be approved or modified by a downstream human inspector. In either circumstance the amount of human labor and decision making involved is greatly reduced over that required for manual grading.

SUMMARY OF THE INVENTION

The present invention in its broadest form is a method of assisting lumber grading. It comprises determining pith position of the log from which the lumber was cut, relative to preselected faces of the lumber, whereby knot orientation may be determined. The method further includes computing the orientation of the knots, determining the effective diameter and location of any knots detected, and estimating their cross sectional area whereby a tentative grade may be assigned to the lumber.

The method involves conveying the lumber past a scanning station. First and second faces of the lumber are scanned to determine the presence or absence of wane, and its location if present. The second face is defined as being opposite and essentially parallel to the first face. At least the first and second faces are further scanned to determine the number and size of knots present on each face. Optionally, the other faces or edges may also be scanned. With the wane and knot information thus supplied by the scanners, the pith position of the log from which the lumber was cut may be computed, relative the scanned faces. With pith position known, knot orientation may be readily determined. The method further includes determining the effective diameter and location of any knots which are detected. The orientation of the knots may be computed and an estimated cross sectional area determined. With this knowledge a tentative grade can be assigned to the lumber.

In its preferred embodiment the method includes a scanning step which can measure localized grain direction as an indicator of the presence or absence of any knots. Preferably this scanning method will determine localized wood fiber angle relative to three mutually orthogonal axes. These fiber angle measurements reveal grain slope disturbances on the lumber which are indicative of a number of defects which include but are not limited to knots. Preferably this scanning step will also determine the presence or absence of any spiky faces on the lumber being scanned. A spiky face is here defined as one which lies on or closely adjacent to a plane which is parallel to a plane defining a diameter of the original log and is likely to contain elongated "spike" knots. Spiky faces may show an exposure of pith or indicate that the pith is included within the piece of lumber being examined.

Normally the scanning steps include making a multiplicity of longitudinally spaced apart scans transversely across each face being scanned. Scanning steps for wane and knot presence/absence may be carried out either sequentially or simultaneously. Preferably, in the present method, they are carried out simultaneously.

It is thus an object of the present invention to provide a method for determining pith position of the log from which a piece of lumber was cut, relative to one face of the lumber.

It is another object to determine pith position whereby the orientation of knots in the lumber may be readily determined.

It is further object to provide a method in which grain slope disturbances on the lumber are indicative of defects including knots.

It is also an object of the present invention to provide a method for estimating location and cross sectional area of knots within a piece of lumber so that a tentative structural grade may be assigned to the piece.

These and many other objects will become readily apparent to those skilled in the art upon reading the following detailed description of the invention taken in conjunction with the drawings.

DESCRIPTION OF THE PREFERRED EMBODIMENTS

Figure 1:
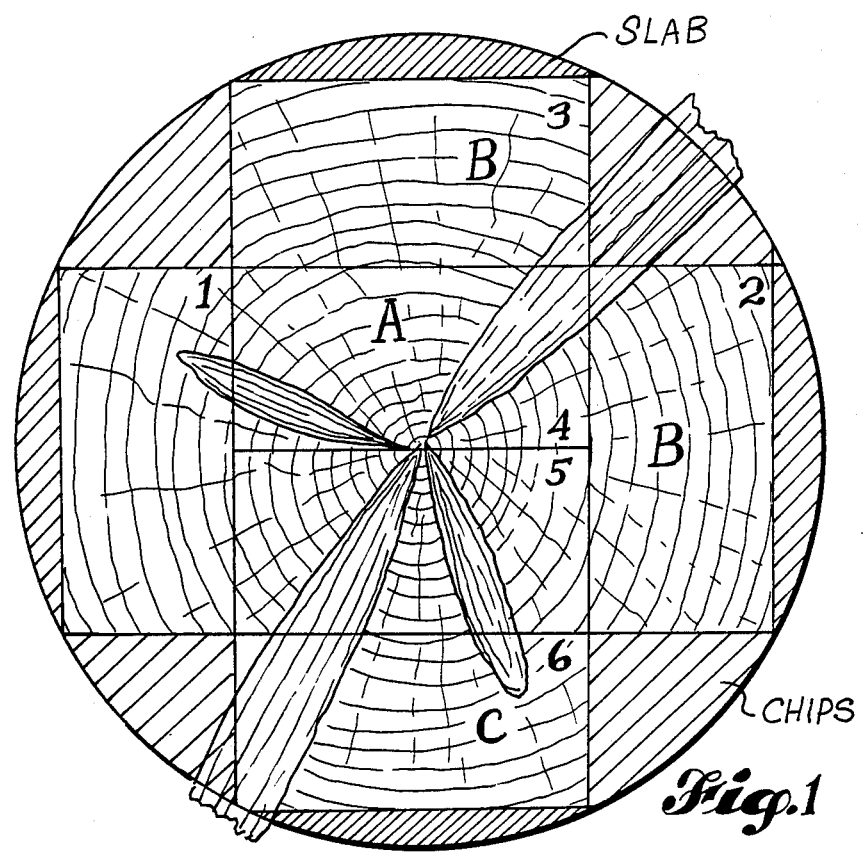
FIG. 1 is a cross section of a log from which six pieces of finished lumber may be obtained.
Figure 2:
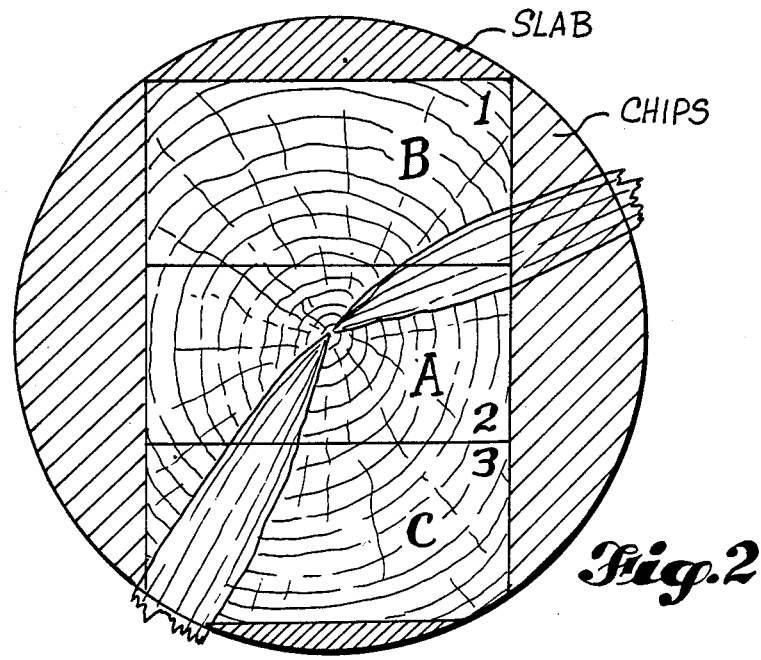
FIG. 2 is a similar cross sectional view of a smaller log from which only three pieces of finished lumber are obtained.

Most of the old growth timber in the United States has now been cut and sawmills are receiving logs having increasingly smaller average diameters. The method of the present invention is most effectively applied to small logs being processed in high speed automated sawmills although it should not be considered as limited to these conditions. Many mills are no longer equipped to handle logs larger than about 50 cm (20 in.) in diameter. More typically mills, especially in the south and southeast portion of the country receive log mixes in which the largest logs are rarely over about 35 cm (14 in.) in diameter. These logs are typically processed by passing them through a first station in which flat faces are created on both sides of the log to produce a cant. The material removed is converted into pulp chips. When logs are large enough, a pair of parallel band saws may remove one or more side boards. FIG. 1 indicates a log in which gang cant and two side boards are produced, in addition to the chips. FIG. 2 shows a smaller log in which only a gang cant is produced. The cants taken from the center of the log are then normally processed in a single or double arbor circular gang saw to produce a number of pieces of lumber. The slabs taken from the outside faces are separately sent to a chipper where the useful fiber can be recovered.

Figure 3:
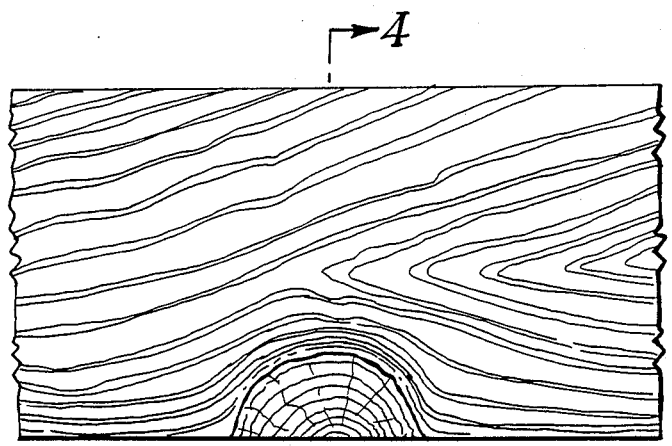
FIG. 3 is a fragmentary view of a portion of the wide face of a piece of finished lumber showing an edge knot.
Figure 4A:
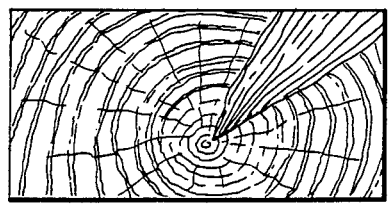
FIGS. 4A through D are cross sectional views taken along line 4—4 of FIG. 3 showing four possible configurations of the knot within the lumber.

Reference to FIG. 3 shows a piece of lumber containing an edge knot. When viewed only from the face shown, there is no information as to how a serious a defect the knot presents. Previous scanner grading methods would assume that the knot is a cylinder projected through the piece of lumber and grade it accordingly. The present method makes no such assumptions. FIGS. 4A through D show four possibilities for the edge knot of FIG. 3. In FIG. 4A the knot originates within the piece. This condition, in which the pith or growth center is enclosed within the piece of lumber, is called "boxed heart." In FIG. 4B the knot merely nicks the edge of the lumber and does not create a serious reduction in strength. However, in FIG. 4C the knot passes entirely through the lumber and occupies a large portion of the cross sectional area. FIG. 4D is essentially the condition that would have been postulated by earlier scanners, where the knot is an approximate cylinder passing through the lumber normal to both wide faces.

Figure 4B:
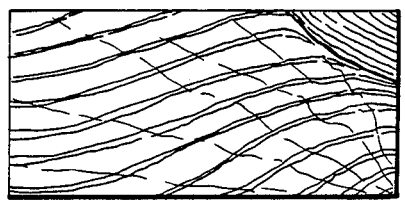
Figure 4C:
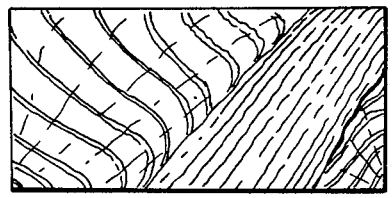
Figure 4D:
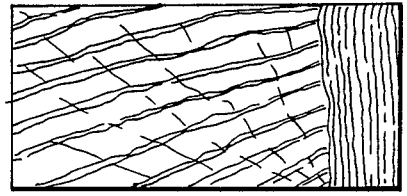

The four possibilities shown in FIGS. 4A through D each represent different knot positions and cross sectional areas and each affect the strength of the board differently at the cross section along line 4—4 of FIG. 3. The condition shown in FIG. 4C is obviously much more serious than that represented in FIGS. 4A or 4B.

Figure 5:
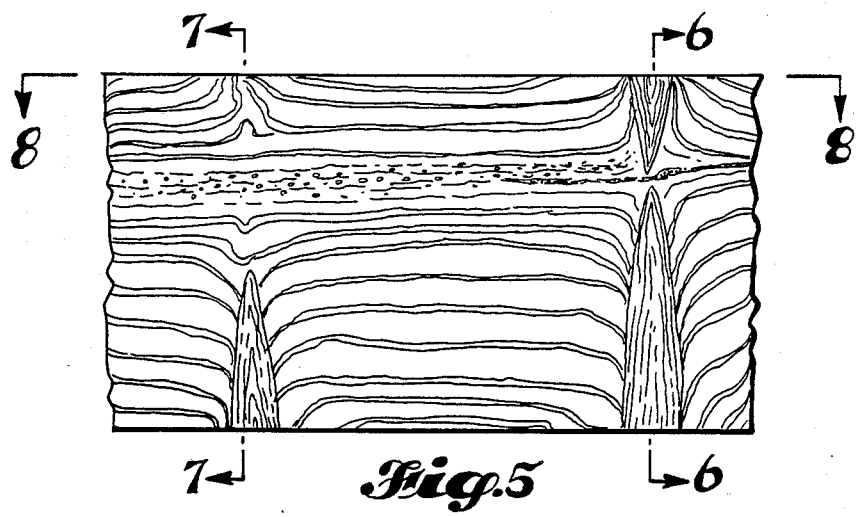
FIG. 5 is a fragmentary portion of a piece of finished lumber showing a spiky face.
Figure 7:
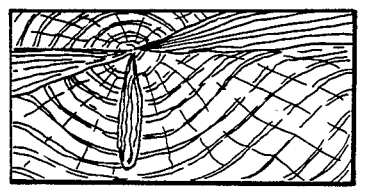
FIGS. 6 and 7 are cross sections respectively taken along lines 6—6 and 7—7 of FIG. 5.
Figure 6:
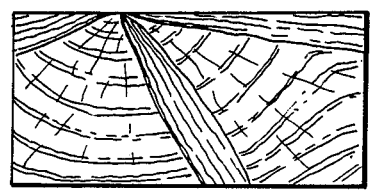
Figure 8:
FIG. 8 is an edge view of the lumber shown in FIG. 5 taken along the lines 8-8.

Whereas those previous scanning systems in the prior art could not in effect "see into the piece," the present inventors have discovered that this can be done quite readily by determining pith location relative to one of the faces of the log. FIG. 4A represents a boxed heart piece in which the pith is contained within the lumber. In FIGS. 4B and 4C, the pith is closest to the upper faces and in FIG. 4D closest to the lower face, although this cannot yet be determined with the information on hand. More information is gained by looking for spiky faces such as are represented in FIG. 5. Here an actual pith streak is seen along the upper right portion of the drawing and it is evident that the pith here must be closest to the upper face. As one moves to the left portion of the drawing, the pith dives into the lumber and it is present as a boxed heart condition in the cross section shown in FIG. 7. Note that one of the transversely oriented knots seen in FIG. 7 does not break through the surface. However, this is shown by grain or fiber angle disturbances noted in the upper left portion of FIG. 5 and these are readily detectable using a scanner of the type described in U.S. Pat. No. 4,606,645.

Figure 9:
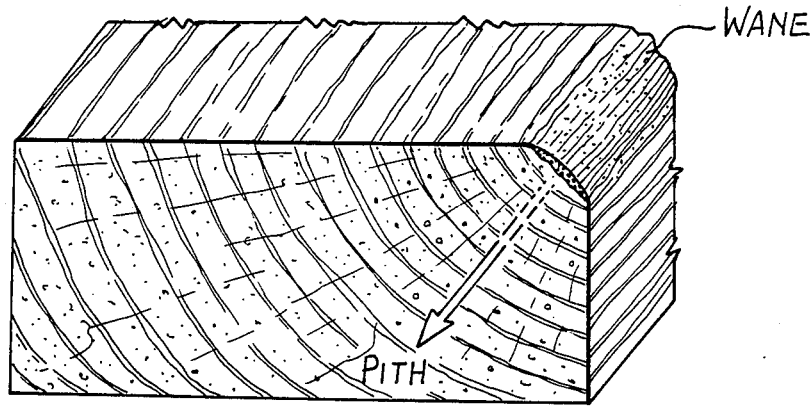
FIG. 9 is perspective view of a piece of lumber showing wane at one corner.

It is relatively easy to determine pith location when wane is present along one or more corners of the lumber being examined. Pith is always found closest to the face which does not contain wane, as is illustrated in FIG. 9.

Figure 10:
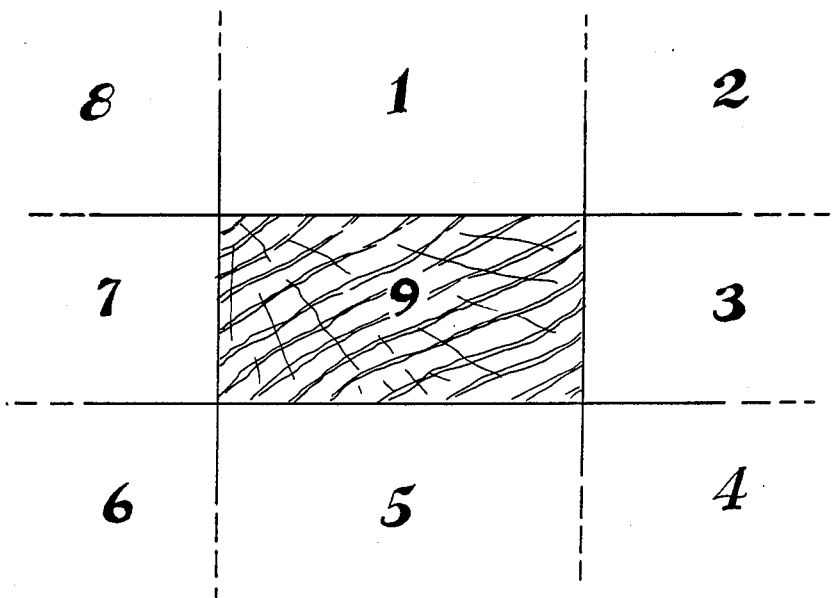
FIG. 10 is a grid showing one way in which pith position can be assigned.

A convenient way to assign pith position is by considering the piece of lumber being examined as located in the center cell of a grid. The pith location can then be assigned to any of the cells. In actual practice, resolution of the type given by FIG. 10 is not normally necessary. It normally suffices to say that the pith is closest to the upper face, the lower face or contained with the lumber itself. In the lumber cut in a small log sawmill pith is located in cells 1, 5 or 9 about 90% of the time.

Figure 11:
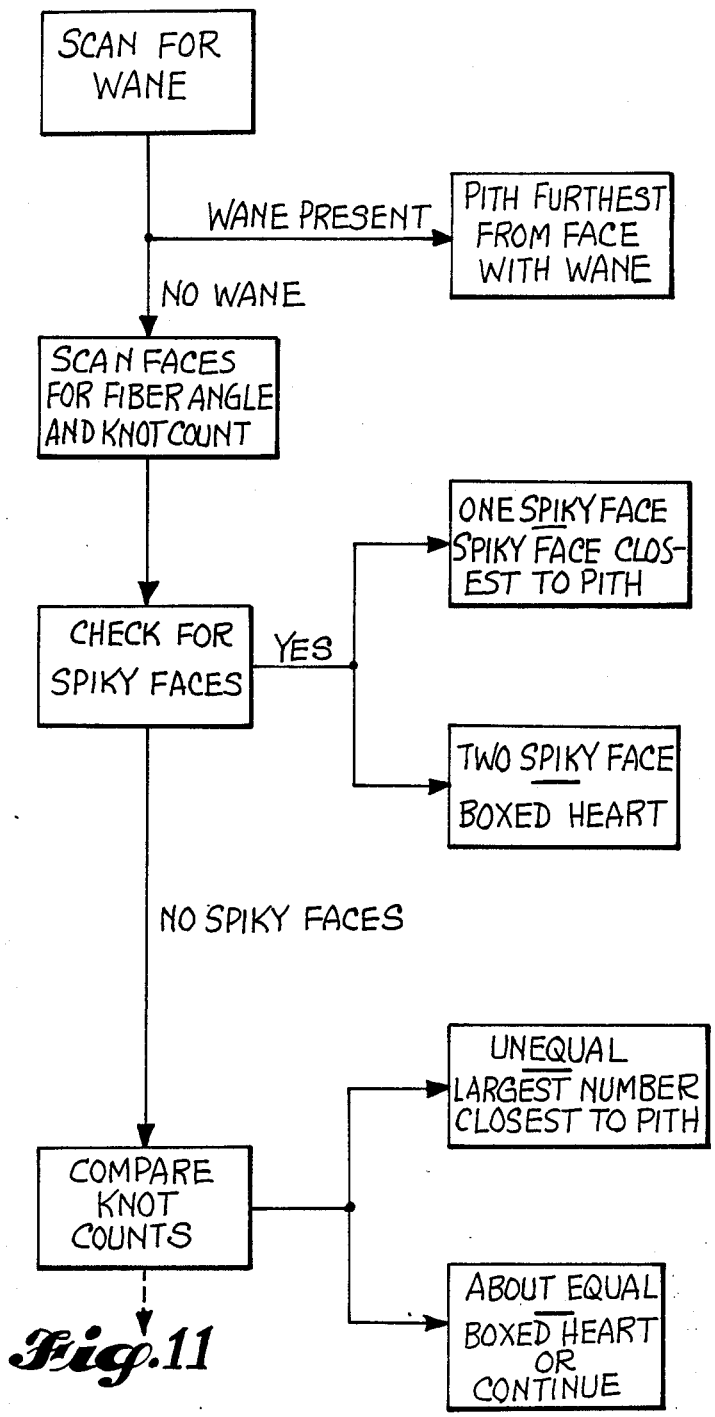
FIGS. 11 and 11A show a block diagram giving decision logic for the present method of assigned pith position.
Figure 11A:
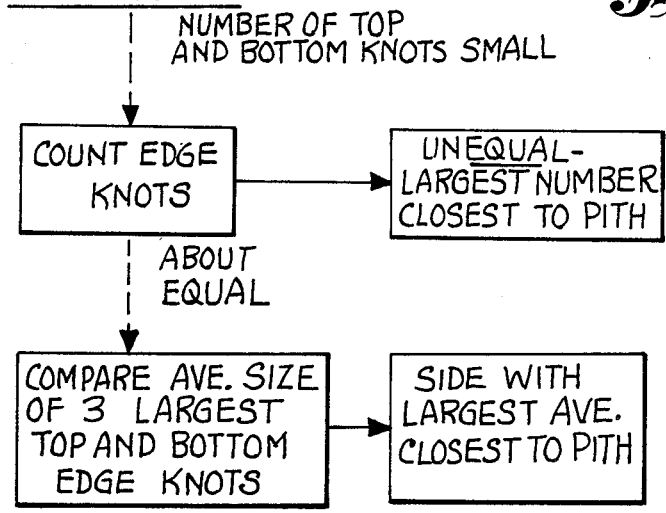

FIGS. 11 and 11A illustrate logic diagrams for determining pith orientation. The corners or edges of the lumber are first scanned for wane. If wane is present, the pith can be assigned as being closest to the face without wane. If no wane is present, additional information must be gained and this comes from the scans which measure grain distortion and knot count of the opposed faces. A first check is made for the presence of spiky faces. If only one spiky face is present, this is closest to the pith. If two spiky faces are present, this is an indicator of boxed heart. However, if no spiky faces are present, knot counts on the respective faces are compared. If these knot counts are significantly unequal, the face with the largest number of knots is closest to the pith. If the knot counts are about equal, this is an indicator of boxed heart. Alternatively, if higher resolution is desired at this point, the additional steps shown in FIG. 11A may be carried out. If the total knot count on both faces is low, edge knots are then counted. If the two faces have significantly different edge knot counts, the face with the fewest number of edge knots will be closest to the pith. On the other hand, if the faces have approximately equal numbers of edge knots, the average size of about three of the largest edge knots on each face is compared. Here the side with the largest average edge knot size is deemed to be the closest to the pith.

Reference to FIG. 1 will show why comparing knot counts on the two faces is an indicator of pith position. The two pieces numbered 1 and 6 have unequal numbers of knots caused by the presence of small limbs which broke off during an early stage of tree growth. Note that the letters shown within several of the pieces of FIGS. 1 and 2 refer to lumber cross sections having configurations as seen in FIGS. 4A through C.

Figure 12:
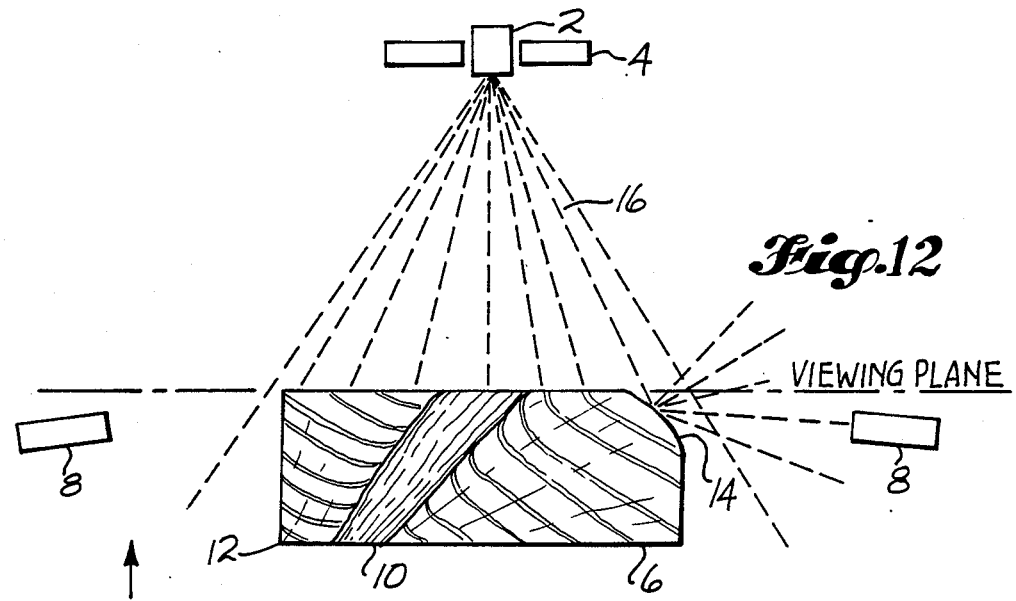
FIG. 12 is a cross sectional elevation view representing one scanning station.
Figure 13:
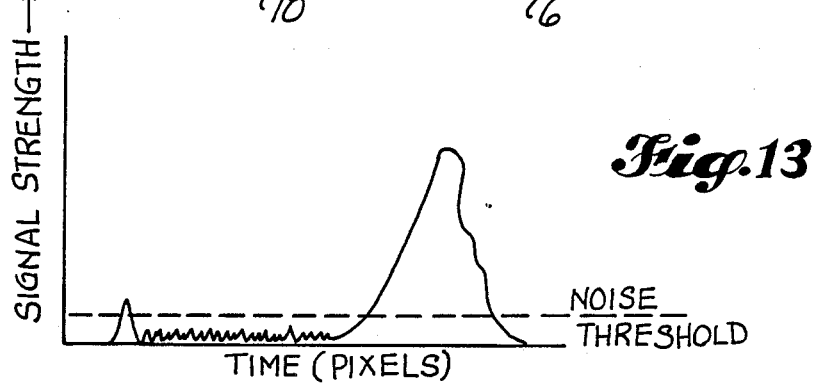
FIG. 13 is a plot of signal strength versus time for the wane scanners used with the apparatus of FIG. 12.

FIG. 12 diagramatically illustrates a scanner employing the present method. The scanner used is the one described in Matthews et al, U.S. Pat. No. 4,606,645. It employs a low power laser 2 surrounded by a ring of photosensors 4. In the present case eight photosensors are used equiangularly spaced around the laser. While higher resolution can be obtained by using a greater number of photo sensors, this has not been found to be necessary for the present purposes. The laser beam is moved transversely across the advancing piece of lumber 6 by an oscillating mirror or lens, not shown. Reflections from the surface of the lumber 6 are picked up by the photosensors 4 where they are interpreted into localized grain angle relative to three orthogonal axes. Wane sensors 8 lie below the viewing plane on each side of the piece of lumber being examined. Where there is no wane present, essentially no signal is picked up by the sensors 8 except for a brief blip at the beginning and end of the scan caused by the eased edges 12 on the lumber. However, when wane is present, the laser beam will be reflected to the appropriate sensor 8 and gives an output as is shown in FIG. 13. Signals from these sensors are preferably fed through logarithmic amplifiers to those signals having lower output will be proportionally amplified more than signals of high output. This enables much more precise location of the margins of wane area 14 on the lumber. The lumber piece 6 also contains a knot 10 and the reflection from this will be clearly picked up by the ring of scanners 4 as a grain angle disturbance. For convenience only one scanner is shown. A similar system will normally be used on the other side of the lumber. Alternatively, a mirror system can be employed so that alternate scans are made on the top and bottom surface using a single scanner.

In one installation lumber was passed by a scanner of the type shown in FIG. 12 at a speed of 350 m/min. (1150 ft/min.). Grain pattern distortions indicative of knots and other defects were clearly indicated by the scanning system. In sawmill tests before the system was fully optimized, correct grade was assigned to the lumber 75-80% of the time. At this time the system was not considering such defects as splits, crook and planar skip. A grader could readily observe these defects and override the system's assigned grade, if necessary.

When working with a reasonably flat grained or tangentially sawn piece of lumber there is a very certain way to determine pith location relative to the face being viewed. Wood fibers, as a general rule, are laid down by a growing coniferous tree parallel to its longitudinal axis or pith. However, at the immediate proximity of branches the fibers tend to sweep outward along the branch rather than remain parallel to the pith. This is shown in FIGS. 4C and 12, and especially well in FIG. 5. Note that when a given face of a piece of lumber is being viewed, as in FIG. 12, if the fibers adjacent to a knot converge, or slope in toward the knot as seen from the viewing location, the pith location is in a direction away from the viewpoint. This is the case for this particular figure. For the converse situation, if the fibers adjacent to a knot diverge, or appear to slope in a funnel-shaped configuration, the pith location is toward the viewing point. The fiber angle orientation can be readily determined using a scanner of the type described in U.S. Pat. No. 4,606,645 and the information entered into the logic sequences of FIG. 11.

Key to the success of the system is the ability to first determine pith position relative to the faces of the board. With this known, knot orientation is indicated. Then with that knowledge, taken with a knowledge of knot size and position indicated by the scanners, knot cross sectional area and location can be determined with considerable accuracy.

It will be evident to those skilled in the art that other scanners can be used for pith position determination besides the scanning system described in U.S. Pat. No. 4,606,645. For examples, one of the earlier noted gray scale scanners could be used for surface knot determination along with a scanner of the type described by Dahlstrom et al for wane indication. However, the inventors believe the system they have described using the scanner of U.S. Pat. No. 4,606,645 to be optimum and to represent the best mode currently known of carrying out their invention.

It will be readily apparent to those skilled in the art that many departures can be made from the method that has just been described without departing from the spirit of the invention. Thus the invention is to be considered as limited only by the following claims.

We claim:

1. A method of determining pith location relative to at least one face of a piece of lumber which comprises:
 conveying the lumber past a scanning station;

scanning at least said one face to determine the direction of wood fiber grain angle relative to three mutually orthogonal reference axes adjacent to any knots which may be present, and identifying said pith location from said grain angle information, wherein said pith location is generally away from the scanner position and within or through the piece of lumber when the fibers adjacent a knot are found to converge toward the knot in a direction toward the scanning position, and pith location is toward the scanning position and outside the piece of lumber when the fibers are found to converge toward the knot in a direction away from the scanning position, said pith location knowledge being useful for determining knot shape and orientation within the lumber as an aid to grading the lumber.

2. The method of claim 1 where further includes scanning at least said one face and an opposing essentially parallel second face of the lumber to determine the presence or absence of wane and its location if present, whereby both the wane and fiber angle information adjacent knots are used to predict pith location.

3. The method of claim 1 or 2 in which said further scanning step includes computing orientation and determining effective diameter and location of any knots detected, estimating cross sectional area of the knots, and then assigning a tentative grade to the lumber.

4. The method of claims 1 or 2 in which said scanning steps include making a multiplicity of longitudinally spaced apart scans transversely across the faces being scanned.

5. The method of claim 2 in which the scanning steps for wane and wood fiber angle orientation are carried out simultaneously.

6. The method of claim 2 in which the scanning steps are carried out sequentially.

* * * * *